US007069227B1

(12) United States Patent
Lintel, III et al.

(10) Patent No.: US 7,069,227 B1
(45) Date of Patent: Jun. 27, 2006

(54) HEALTHCARE INFORMATION NETWORK

(75) Inventors: Albert G. Lintel, III, Atlanta, GA (US); Joseph A. Vescio, Alpharetta, GA (US); Joseph L. Helmick, Atlanta, GA (US)

(73) Assignee: Zansor Systems, LLC, Atlanta, GA (US)

( * ) Notice: Subject to any disclaimer, the term of this patent is extended or adjusted under 35 U.S.C. 154(b) by 540 days.

(21) Appl. No.: 09/496,783

(22) Filed: Feb. 3, 2000

Related U.S. Application Data (60) Provisional application No. 60/119,041, filed on Feb. 5, 1999.

(51) Int. Cl.
*G06F 17/60* (2006.01)
(52) U.S. Cl. ...................... 705/4; 707/1; 707/10; 705/2
(58) Field of Classification Search .................. 705/4, 705/2, 3; 707/1, 10, 102, 3, 500
See application file for complete search history.

(56) References Cited

U.S. PATENT DOCUMENTS

| | | | | |
|---|---|---|---|---|
| 5,253,164 A | * | 10/1993 | Holloway et al. | 705/2 |
| 5,359,509 A | * | 10/1994 | Little et al. | 705/2 |
| 5,826,269 A | * | 10/1998 | Hussey | 703/27 |
| 5,890,129 A | * | 3/1999 | Spurgeon | 460/100 |
| 5,915,240 A | * | 6/1999 | Karpf | 705/1 |
| 5,946,659 A | * | 8/1999 | Lancelot et al. | 705/2 |
| 5,987,480 A | * | 11/1999 | Donohue et al. | 707/501.1 |
| 5,995,939 A | * | 11/1999 | Berman et al. | 705/3 |
| 6,343,271 B1 | * | 1/2002 | Peterson et al. | 705/4 |

FOREIGN PATENT DOCUMENTS

WO    WO 9512812 A1    5/1995

OTHER PUBLICATIONS

"Personal Librarian 3.0 for windows Revamp Appeals to End-User," InfoWorld, Aug. 31, 1992.*
"New Company Revolutionizes Healthcare Information Market," Business Wire, Dec. 16, 1998.*
("Reducing Medicaid spending on long-term care," The Business Journal, May 12, 1997, vol. 11, issue 10.*
Miller Freeman, What to do when a pharmacist suspects a script is forged, Mar. 31, 2001, Pulse, Iss. 00486000, p. 76.

* cited by examiner

*Primary Examiner*—Joseph Thomas
*Assistant Examiner*—Robert W. Morgan
(74) *Attorney, Agent, or Firm*—Anderson, Levine & Lintel, LLP (57) ABSTRACT

A healthcare information network provides a global database at a central information system which is synchronized with local databases at respective healthcare provider offices. The local database are used by the healthcare providers for confirming patient and healthcare information. As patient and health plan information is added, updated or deleted from any of the local databases, files are generated to update the global database. The proposed changes to the global database are verified and the global database is modified. Modification of the global database is memorialized in a repository which is then used to produce SQL commands to update each of the local databases so that they are synchronized with the global database.

7 Claims, 11 Drawing Sheets

| Zansor Patient Referral | | | ¬ □ X |
|---|---|---|---|
| File Send Configure Window Help | | | |

Select Carrier and Plan        ¬ □ X

| Back | Next | Message |
|---|---|---|

— 162

| | Carrier Name | Plan Name | Type |
|---|---|---|---|
| | Self Pay | Self Pay | self |
| | Aetna | Aetna US-Healthcare QPOS | POS |
| | Aetna | Aetna US Heathcare EPO | EPO |
| | Aetna | Aetna US Heathcare HMO | HMO |
| | Aetna | Aetna US Healthcare PPO | PPO |
| | Aetna | Aetna US Heathcare Choice PPO | PPO |
| | Affordable | Affordable Healthcare Compare | PPO |
| | America Health | America's Health Plan | PPO |
| | Americaid | Americaid | PPO |
| | American Medical | American Medical Plan GA | PPO |
| | Anthem | Anthem | POS |
| | | | |

| Referral Listing | | | | X |
|---|---|---|---|---|
| Created | Status | Authorization # | Patient Name | Specialist Name |
| 1/10/00 3:23P | Sent | 123742947 | Smith, Homer | Abu, John |
| 1/10/00 2:10P | Sent | Dfa827 | Doe, John | Payne, Max |
| 1/09/00 | Sent | 939KK | Atest, I.M. | Cohen, Al |
| | | | | |
| | | | | |
| | | | | |
| | | | | |
| | | | | |
| | | | | |
| | | | | |

| Sort | | View/Print Form | View/Print Report |
|---|---|---|---|

```
Zansor Patient Referral                                    ⌐ □ X
File  Send  Configure  Window  Help
```

Fill Out Referral Form                          ⌐ □ X    Print

| Back | Next | Select Primary Care Physician |
|      |      | Tookay, V. (AetnaHMO 325728945729857) ▽ |    Return 166    162
                      Aetna US Healthcare
                      Electronic Referral
                      Entry Sheet
                                                              ⎯ 170

Envoy ID         [                    ]
Carrier Code     [                    ]
Your Aetna US Healthcare Provider ID   [            ]
Aetna US Healthcare Member ID or SSN   [            ]

Referred Provider ID   [                ]
Referred Facility ID   [                ]

Diagnosis Code(s) or Group(s)   [    ][    ][    ]

Procedure Code(s) or Group(s)   [    ][    ][    ]

Number of Visits [    ]  Appointment Date [           ]

Place of Service Code [    ]
         1- Office Visit      3- Outpatient
         2- Inpatient         4- Same Day Surgery
Comment Code
  ☐ 1- Call me            ☐ 13- Perform procedure on left side
  ☐ 2- Letter to Follow      14 – Bilateral procedure

HEALTHCARE INFORMATION NETWORK

CROSS-REFERENCE TO RELATED APPLICATIONS

This application claims the benefit of the filing date of co-pending provisional application U.S. Ser. No. 60/119,041, filed Feb. 5, 1999, entitled "Healthcare Information Network" to Lintel et al.

STATEMENT OF FEDERALLY SPONSORED RESEARCH OR DEVELOPMENT

Not Applicable

BACKGROUND OF THE INVENTION

1. Technical Field

This invention relates in general to health care and, more particularly, to a healthcare information system.

2. Description of the Related Art

A significant problem in providing health care services is the confirmation process which ensures that a patient's health plan coverage is appropriate to cover the health services to be rendered. A health plan has certain characteristics that define the benefits for the eligible patient and informational requirements for the eligible patient to obtain those benefits. The following are typical:

A. Effective dates or period of coverage
B. Cost sharing
  1. Co-pay office visit
  2. Co-pay emergency visit
  3. Deductible
C. Covered services
  1. Approved Healthcare providers
    a. Primary care physicians
    b. Specialty physician
    c. Hospitals
    d. Pharmacies and suppliers of medical equipment
    e. Free standing laboratory and radiology facilities
    f. Home health providers
    g. Long-term and special care centers
  2. Procedures or diagnostic test based on clinical criteria
  3. Formats for obtaining authorization for referral to approved providers
    a. Printed forms that are filled in and faxed
    b. Telephone processes using dialtone input
    c. Telephone process using person to person information exchange
    d. Web based forms
    e. Direct electronic data interface devices (EDI).
  4. Information required for referral authorization
    a. Primary physician name
    b. Primary physician plan ID number
    c. Primary physician address, fax and phone number
    d. Referred to provider's name
    e. Referred to provider's plan ID number
    f. Referred to provider's address
    g. Diagnostic and procedure codes
    h. Member's plan ID, name and date of birth
D. Billing information
  1. Employer sponsor
  2. Responsible person or policy holder
  3. Persons covered under policy holder
  4. Mailing address
  5. Approved format
    a. Printed forms
    b. Electronic claims submission (EDI)
  6. Time period for claim submission
  7. Identification numbers (policy and group)

(A), (B) and (D.1–4) are usually printed on the patient's insurance card. Most other information is usually contained in the manual the provider receives after contracting with the given health plan. (C.1.a–c) may be in a manual carried by the patient and (C.2.) may be in the form of instructions on contacting the plan with medical information before the procedure or test is approved.

Ideally, a patient presents to the provider with the insurance card. The patient is billed for the co-pay on the card and the remaining deductible. If a referral is required, the patient is sent to the approved provider and the bill is submitted, as instructed in the manual. In practice, the following errors, omissions or delays occur:

A. The patient may give or present information that he is covered when he is not.

B. The patient may not have a card, the card may be out-dated, or invalid.

C. The patient may be on a contracted health plan, which is administered by a third party or employer, and has different billing information than the typical health plan.

D. Determining approved providers for referral:
  1. Changes may have occurred since the last printing of the manual.
  2. Providers may be listed only in the patient's manual, which is unavailable.
  3. Providers may be listed only by county, without regard to specific location or hospital affiliation, if admission is required.

E. Billing information may have changed since the last printing of the manual.

F. Clerical staff may introduce errors or omissions by manual data input.

Traditionally, the insurance information for the patient is entered manually in the patient record when he presents to the office. After the patient's visit, his financial obligation is billed to him and a claim is submitted to the carrier according to written instruction. The acceptance or rejection of the submitted claim usually determines eligibility or verification that a patient is on a health plan. This occurs either by mail or electronic claims submission. It may also be done by telephone, which tie up staff from other duties.

Health insurance plans that manage patients' care do so by restricting the patient to providers approved by the plan. In general, when a patient requires care beyond that of the primary physician, the plan will reimburse those providers who are approved by the plan for referrals made by the primary physician. The process whereby an insurance plan acknowledges this care will be reimbursed is generally referred to as "authorization". Authorization may require only that the primary physician fax or mail a form containing information to them, or it may require the submission of specific information and issue a specific authorization number prior to approving reimbursement for services requested by the referral.

Each plan has a specific process and may allow multiple processes (C.3.). When a referral is suggested to a patient by their primary physician, the most common practice is for the patient find, and make an appointment with, a plan approved provider. After the appointment is made, the patient calls the primary physician's office with the name of the provider and the appointment date. The primary physician then completes the authorization process required by the plan and faxes the authorization number to the referred to provider. In most cases, the referred to provider will require documentation of authorization before accepting plan reimbursement for services provided to the patient.

In this regard, (C.3.a.) may be supplied by the insurance plan as printed forms which the provider copies, completes and then faxes back to the insurance plan. (C.3.b–c) are usually written procedures supplied to the provider by the plan and often with a printed template that can be copied and used for exchanging information over the telephone. (C.3.d) is software or procedures for using a web base browser that enable a provider to complete the referral on a "web page". (C.3.e) are proprietary input devices such as a "swipe card reader" terminal that use an EDI connection.

Completing the authorization process involves many time consuming procedures involving required information (C.4.). When submitted forms are used, they are usually completed by hand since many require boxes to be "blacked out" to be read later by optical character recognition devices. Redundant information must be manually entered on each form (4.a–c). Other types of information require that manuals be searched for the various numbers(4.d–g). For authorizations requiring a specific authorization number from the plan, the staff usually contacts the plan by phone using a manual dialtone entry procedure. Most dialtone processes will terminate unless the required numbers are rapidly entered in a certain sequence. To avoid termination, the staff must fill out a form or template to prepare for entering the information. Web based forms require Internet dialup for each session unless the office has a dedicated connection. EDI devices serve only a limited number of plans participating with companies providing the necessary equipment.

This system has significant adverse consequences. For the confirmation of health plan eligibility, real time confirmation (typically by telephone), and referral authorization, consumes the staff time of both provider and health plan and confirmation by claims submission increases the billing cycle and produces duplication of effort. The manual data input increases time spent by patient and staff and produces a higher error rate than automated entry. Incorrect co-pay or deductible results in under and over-charging requiring rebilling and refunding procedures. Incorrect patient address results in delayed or non-collection of charges. Incorrect billing information results in the claim being returned and delayed, rebilling procedures, and sometimes loss of charges due to time factors. Inability to quickly and accurately identify approved providers for referral may results in increased staff work to search and call for information and delays in patient care. Referral to a non-approved provider may result in increased staff work required correcting the referral, non-payment by the health plan to the "non-approved" provider who then charges the patient and higher than usual charges from the "non-approved" provider made to the health plan.

Incorrect information provided by a patient at one provider may be repeated at other providers. This results in a cycle of redundant information correction, at multiple providers, for a single error.

A limited number of online systems (Internet or direct dial-up) provide the ability for a provider to connect with a database server that has some of the information listed in the first section. These databases only contain information that is shared with them by a health insurance carrier or plan which has an agreement to do so. Updated information is supplied only by the insurance carrier or health plan. Healthcare providers access these systems when the patient arrives at the office, or after the patient has been treated.

These online systems also have server-related problems. The server or connection may be unavailable or slow, and time is spent waiting for connection, unless dedicated line is purchased. The patient's health plan may not share information with the online system, and the patient's health plan may not regularly update information with the online system. Further, the information is typically accessed through a browser interface, which can not automatically export the information into their office management software, requiring increased staff time and error due to manual data input. Referrals made by web browsers must then be printed and manually faxed to the referred to provider.

The speed, and allocation of staff resources, required to give medical care to a patient is dependent upon the accuracy and availability of information pertaining to patients' health plans. Further, the provider's profit for providing medical care is directly related to both the amount of staff resources needed to provide this care, and the efficiency and timeliness of collecting payment for these services.

Current systems suffer from the inability to give the health care provider consistent, timely and accurate information regarding patients' insurance status and requirements. The traditional system can only obtain the correct information after the claim has been submitted or by utilize staff to make telephone calls. Online systems have information that is limited to the health plans agreeing to share data, and is therefore fragmented. It is also subject to disruption in the telecommunications network and restricted in interfacing with the providers' software systems.

Therefore, a need has arisen for a health care information system which provides accurate and timely patient information.

BRIEF SUMMARY OF THE INVENTION

In the present invention, a healthcare information system comprises a central information system having a global database and a plurality of provider office systems. Each provider office system includes a local database and processing circuitry for accessing the database for insurance information related to a patient's insurance plan, generating revisions to the insurance information, and uploading the revisions to the central information system. The central information system includes update circuitry for receiving the revisions from each of the provider office systems and generating updates to the local databases of all of the provider office systems responsive thereto.

The present invention provides significant advantages over the prior art. If any healthcare provider in the network encounters inaccuracies or omissions in their local database, that information is automatically uploaded to the central information system for modification of the global database after verification. Accordingly, each provider in the network benefits from the updates or corrections attributable to any provider in the network. As a result, highly accurate and up-to-date information is available to all healthcare providers for various purposes, including eligibility and benefits verification and referral authorization.

BRIEF DESCRIPTION OF THE SEVERAL VIEWS OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

The present invention is best understood in relation to FIGS. 1–10 of the drawings, like numerals being used for like elements of the various drawings.

Figure 1:
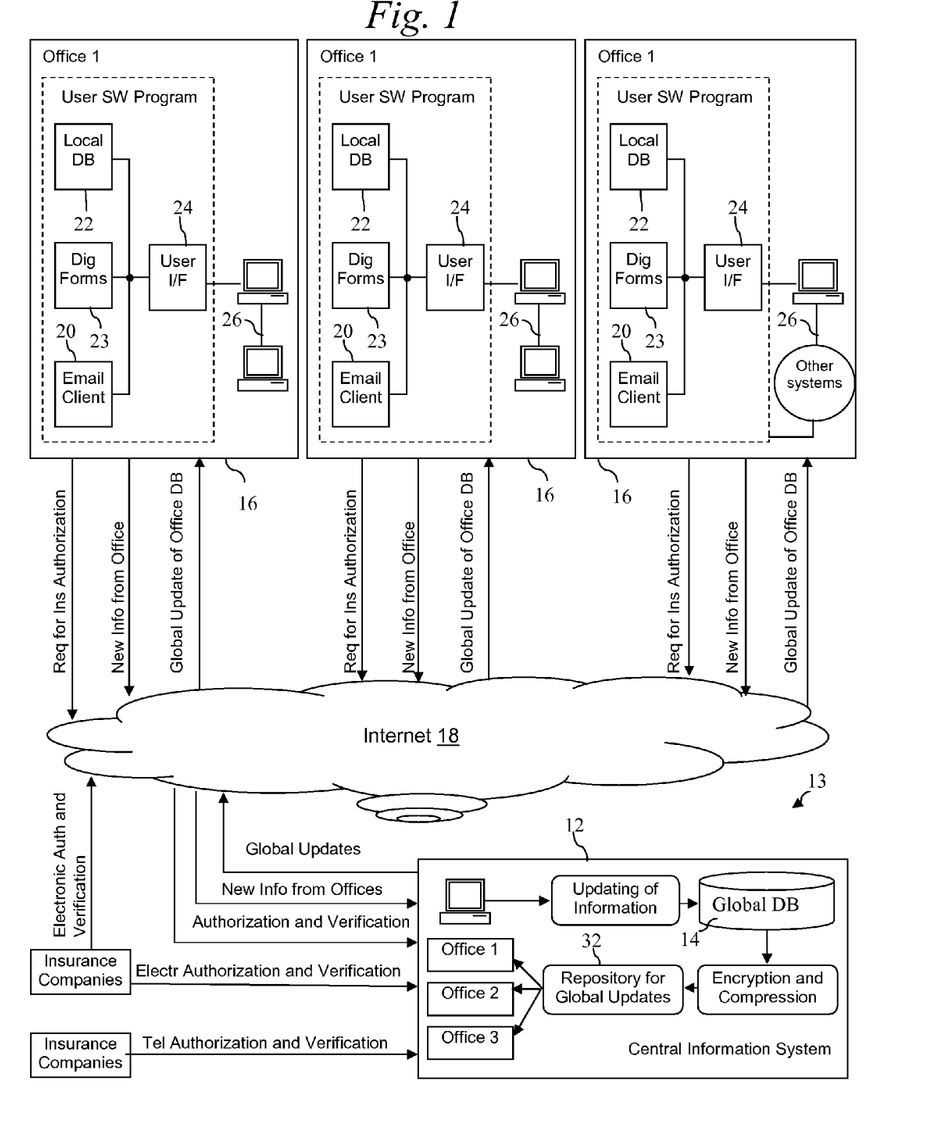
FIG. 1 is block diagram of a healthcare information network.

FIG. 1 illustrates a overall diagram of a healthcare information network 10. A central information system 12 associated with a call center 13 has a global database 14. Office systems 16 are connected to the central information system 12 through the Internet 18. Each office system 16 includes an e-mail program 20 for receiving and sending information, a local database 22 and a healthcare information system 24. Optionally, the office system can have an external link program 26 to link database information to different computers 27 or an internal link program 28 to link database information to other programs 30 on the same computer.

In operation, the healthcare information system 24 is a computer program that does several related things for a doctor's office. Basically, it looks up non-medical information about a patient's insurance plan from the local database 22 stored on the computer (or on another computer in the network). When the patient checks in, and tells the receptionist his or her name, the receptionist will type in a few letters of the last name and the computer will reveal the insurance information and address—all the things would usually be filled in by hand. It will also tell if a given patient is actually covered by a certain insurance plan. In the office, if the patient needs a referral, the staff will use the program, at a computer terminal, to look up the specialist, pharmacy or lab that is covered under his insurance plan. When the patient leaves, office staff will use this program to find the correct billing addresses, co-pay and deductible. This will avoid the bill being returned from the wrong address and delaying payment, or rebilling due to incorrect co-pay or deductible.

The information that is being looked up is stored locally in the office systems 16 as a database or table. Where multiple network computers in an office system 16 are used with the healthcare information system 24, one computer on the network will store the local database 22. The healthcare information system program 24 accesses this database, and displays information about a patient's insurance on the computer screen. Every day (or other period determined to be appropriate), the healthcare information system 24 in each office (or a designated one of the healthcare information systems in an office with multiple networked computers) connects to the Internet (or other telecommunications medium) by modem or other communications device in order to synchronize its local database 22 with the global database 14. In the preferred embodiment, changes to the local databases 22 are made using a binary file attached to an e-mail (such as a POP3 e-mail system); the binary file contains SQL commands to modify records in the database for synchronization. Other ways of communicating the synchronizing information could also be used. If there is an e-mail, the binary file is downloaded into the computer and the binary file is executed. This way, the office information in the local database 22 is always up-to-date within two days.

Sometimes, when the program looks up information (like a patient's health plan or patient specific information), it will not be in the office database on their computer, or the information may be incorrect. When this happens, the health information system sends this new or modified information obtained at the office system 16 to the central information system 12 by e-mail. Changes are generally maintained in a single file to be sent to the central information system at the end of the day.

The call center 13 uses skilled workers to verify and correct information that enters the feedback loop from the providers. The call center operators can be located anywhere that is appropriate and can communicate with the call center through an Internet connection. When the call center 13 receives an e-mail from one of the office computers 16, the database is updated, which may require that the central information system (automatically or manually) contact the appropriate insurance carrier and obtain or confirm information about health plan and make sure the patient is on the plan. The information which requires confirmation can be sent via e-mail to the first available operator or by other criteria, such as the type of information involved or by the specific health plan or coverage type. The new information is then added to the central information systems global database 14.

As information is modified in the global database 14, triggers are generated which write SQL commands (inserts, updates and deletes) to a repository 32. The repository 32 thus documents all changes made to the global database 14. At predetermined intervals, the repository 32 is closed and the SQL binaries are generated for each of the local databases 22. The binaries for some or all of the local databases on the system may be different, since the databases which have sent data modification messages to the central information system will be different from other local databases. A new repository is started for the next group of changes. If the local databases are small relative to the speed of transmission (for example, if the healthcare information system is being used only for referrals), the entire database 22 can be replaced as necessary.

In the preferred embodiment, each e-mail is encrypted with a office-specific private key. This provides security for the patient information being sent on the Internet and keeps an e-mail intended for one office from inadvertently, and possibly incorrectly, updating the database of another office. The information may also be compressed for faster transmission.

When the offices' computers check for new information the next day, they will all get the information necessary to update the local databases 22 to the global database 14 as of the time the repository 32 was closed. Any patient or plan added by any one of the offices in the system the previous day will be available to all offices in the system. The staff is then able to view patient or health plan information on the computer screen if any one of the local databases in the system has this information.

If a change is related only to an element unique to the individual (such as a home address), then all providers on the system have that corrected information available for this individual. If the change is related to an element that is shared by many individuals (such as a change in a health plan co-pay), then all providers on the system have the corrected information for all individuals sharing that element (co-pay). For example, assume a new employer arrives in the area with an accepted health plan, but different co-pay and billing address. Currently, each provider who sees a patient on this plan, for the first time, is subject to all procedures and consequences of dealing with the new information requirements (i.e. calling the health plan for information or incorrectly billing). Under the inventor's system, the first provider in the system who saw a patient on this plan would not find the employer listed on the office database. This new employer and other data would therefore be uploaded to the call center where complete information would be obtained and verified by the health plan sponsor or employer. This information would then be fed back to all the providers on the system, precluding further procedures or consequences.

Since the local database 22 in each office includes the most up-to-date information, it may be desirable to share the information with other computer programs used by the office. Accordingly, the local database 22 may be linked to these other systems, either by porting or linking the information to another computer (which may be necessary when the other system uses a different operating system than the healthcare system) or by providing software to port or link the information to another database on the same computer.

The present invention overcomes deficiencies in current systems by two structures that combine to form a unique process of information sharing: 1) a locally residing, user database that is updated by e-mailed SQL instructions to "mirror" a global database and 2) an electronic call and administrative center that collects and confirms information, discrepant to the local database, which is then used to update the global database. This process serves to continually produce information that is more complete and accurate.

SQL instructions (or similar instructions) provide an efficient alternative to downloading the entire database for the purpose of updating, especially for larger databases. Because a health provider's office system 16 is usually faster and more reliable than an online connection, using a local database provides superior performance with less downtime. A local database 22 is also more easily configured to interface information to other office systems without manual effort. The office database may be accessed by a user interface that only allows "drop-down" selection for less complicated operation. All typed or "free text" information could be sent to the call center for verification before being downloaded back to the providers' office system 16 for final entry. This ensures that patient data, when exported to other office systems, has the least chance of causing a propagation of error.

Conceptually, the system functions as a shared feedback loop, which accumulates relevant health plan information on all patients presenting to all providers in the system. As more patients enter the system, an increasingly complete database of health plan information and eligible enrollees develops. The completeness of the database increases with both time and the relative number of providers in the system. Data sharing by insurance companies 34 can be used to increase completeness (either by sending information electronically or providing tapes or printed materials to be loaded at the call center), but this effect diminishes as the former two factors increase. Therefore, the system becomes self-sustaining with only the participation of the providers who are rendering care to the patient.

Figure 2:
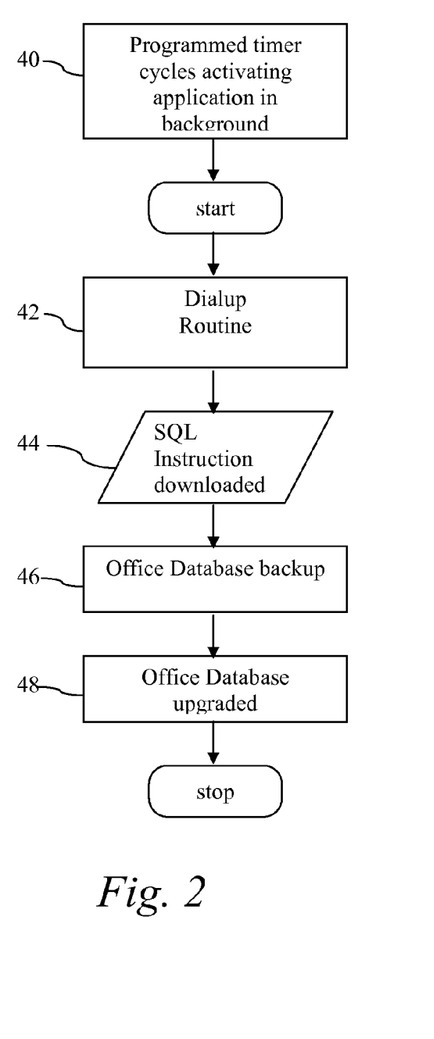
FIG. 2 is a flow chart describing operation of an office download routine.

Flow diagrams describing basic operation of the system are provided below. In FIG. 2, an office download program is shown for incrementally updating a local database 22. In step 40, a timer on the office system 16 initiates the update routine. In step 42, a dialup routine creates a connection to an e-mail server associated with the office system (some technologies such as cable modems and DSL do not require a dialup). In step 44, the SQL instructions from the central information system 12 are downloaded as an attachment to an e-mail. The current local database 22 is copied as a backup in step 46 and the SQL instructions are executed to update the local database 22. These instructions synchronize the local database 22 to the global database 14.

Figure 3:
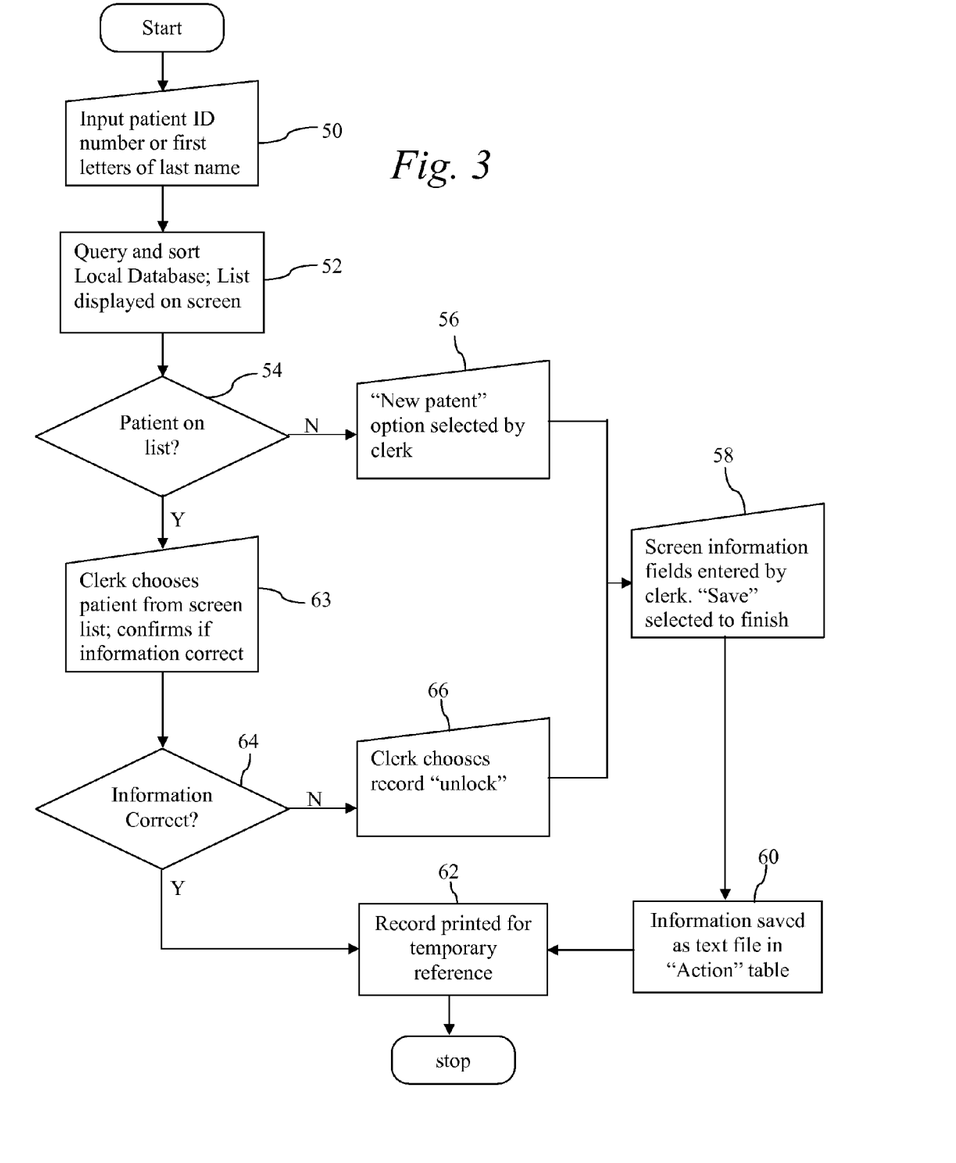
FIG. 3 is a flow chart describing operation of an office patient information routine.

FIG. 3 illustrates a flow chart describing the accessing and updating of information in the local database 22 by the healthcare providers. In response to an input of a patient ID (or all or part of the patient's name) in step 50, insurance information for the patient is retrieved and displayed in step 52. If the patient is not in the local database in decision block 54, a new patient entry is made in step 56. After saving the information in step 58, the new information is stored in a record in a file (the "Action" table) in a text format (step 60). The record may be printed for temporary reference in step 62. Returning again to decision block 54, if the patient has an entry in the local database 22, but the information is incorrect in blocks 63 and 64, the user may unlock the record for modification in step 66. The modification affects only the local database 22 for that particular healthcare provider. Changes to the information are saved in step 58 in the Action table. At a designated time, the Action table is uploaded to the central information system 12, where it is verified and used to update the global database 14 (see FIGS. 5 and 6).

This healthcare information system program includes the main graphical interface with the clerical end-user in the physician's office. The preferred interface is a "form" type, which queries the local database 22, for the patient's record. If the record is found, and correct for the patient, it may be printed as part of the patient's chart for the visit, or may be sent to other office programs which use the information. If the patient is not found, or incorrect, the new information is entered into the same screen. This record is then saved in a separate file as "new". This "new" table is sent to central information system 12, daily, for verification of information. A particular embodiment for entering information is shown in connection with FIG. 9.

Figure 4:
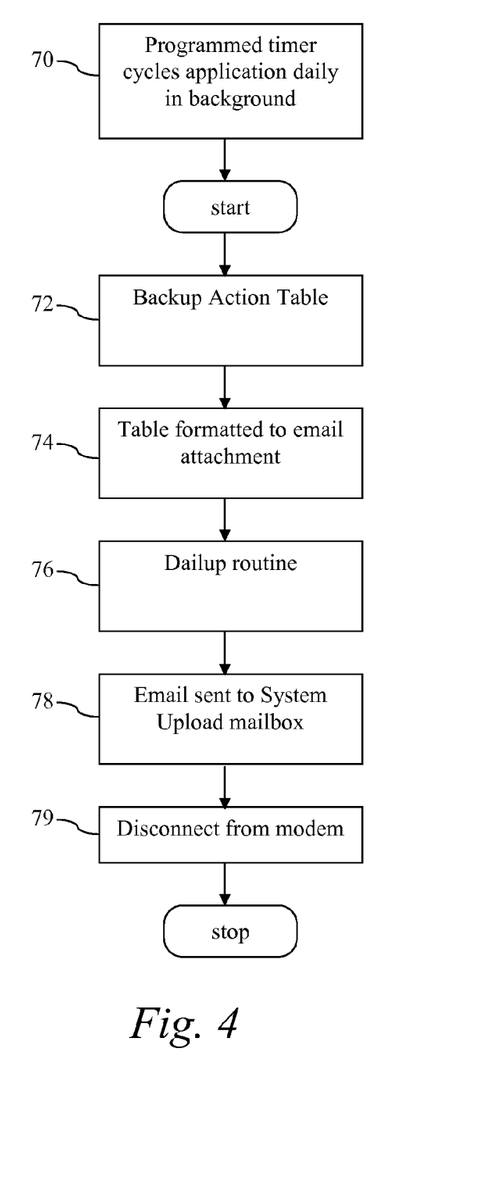
FIG. 4 is a flow chart describing operation of an office upload routine.

FIG. 4 illustrates an office upload routine. In step 70, the upload routine is initiated responsive to predetermined time criteria (typically, after office hours). In step 72, the Action table is copied to a backup. In step 74, the Action table is attached to an e-mail addressed to a mailbox associated with the central information system 12. The e-mail client accesses the Internet in step 76 and sends the e-mail in step 78. In step 79, the e-mail client disconnects from the Internet (if necessary).

Figure 5:
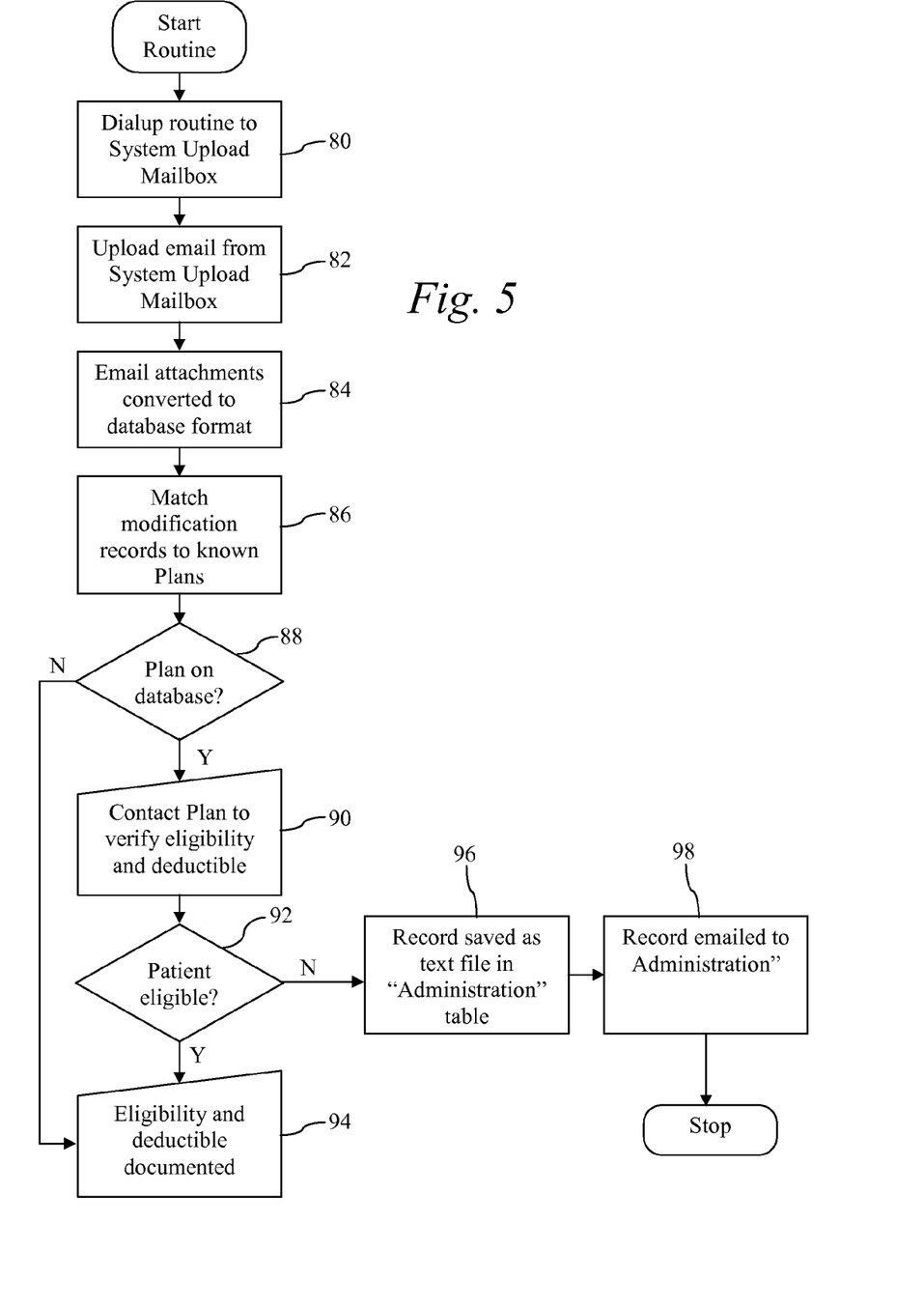
FIG. 5 is a flow chart describing operation of an operator verification routine.

FIG. 5 illustrates an operator verification routine for patient eligibility and benefit modifications and additions. This program uploads new and modified records, originating from the providers' office, via e-mail to the central information system 12. In step 80 the routine is initiated based on predetermined time criteria. In step 82, the central information system retrieves e-mail from a mailbox in an associated mail server. Attachments to the retrieved e-mails are converted to a desired database format in step 84. In step 86, the various modifications are matched with plans in the global database 14 to determine whether the modification is for a new plan or is a modification of existing information. In decision block 88, if the plan is in the global database 14 (i.e., a modification), the plan is contacted (for example, manually by phone or automatically through an Electronic Data Interchange, or EDI, connection) to verify eligibility and deductible information in step 90. If the patient is eligible in decision block 92, the patient's eligibility and deductible are documented in step 94. After documentation in step 94, or if the plan is not on the database in decision block 88 or the patient is not found to be eligible in decision block 92, the outcome is stored in an Administrative Table (step 96) which is e-mailed to an the Administration department which makes the final changes to the global database in step 98.

The routine shown in FIG. 5 preferably provides a graphical user interface to match "new" records with the type of information that needs to be verified or obtained. Information that can be verified at the skill level of the operator (such as determining if the patient is eligible for the plan) is completed and documented here. Records containing information above the operator's skill level (if the plan is not in the database or eligibility cannot be verified) are sorted out. All records are routed to administration for further work and entry into the global database 14.

Figure 6:
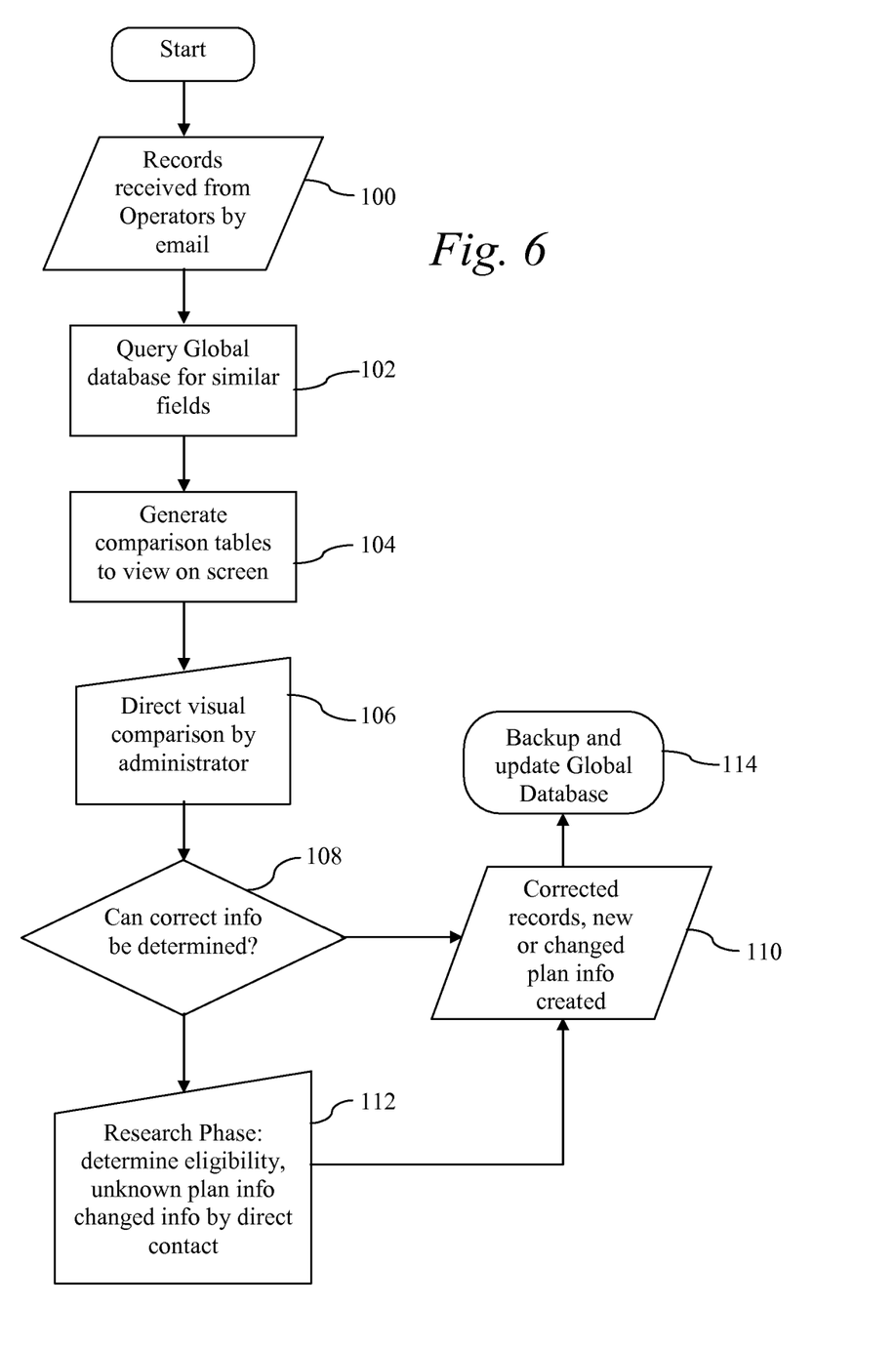
FIG. 6 is a flow chart describing operation of an administrative verification routine.

FIG. 6 illustrates a flow chart describing an administrative database routine. In step 100, the records from the Administrative Table generated in FIG. 5 are received by the Administrative department. The global database 14 is queried for matching records to compare with the records in the Administrative Table in step 102. In step 104, the result of the query is used to generate comparison table to view on screen. In step 106, administrators compare the data from the Administrative Table with the comparison tables. If the modification/addition information can be verified by a visual inspection (decision block 108), records for changing the global database are created to include the new or changed information in block 110. If the information cannot be verified, further research is performed in block 112 prior to generating the new/modified records in step 110. After backing up the global database 14, the new/modified records from step 110 are used to update the global database 14 in step 114.

Figure 7A:
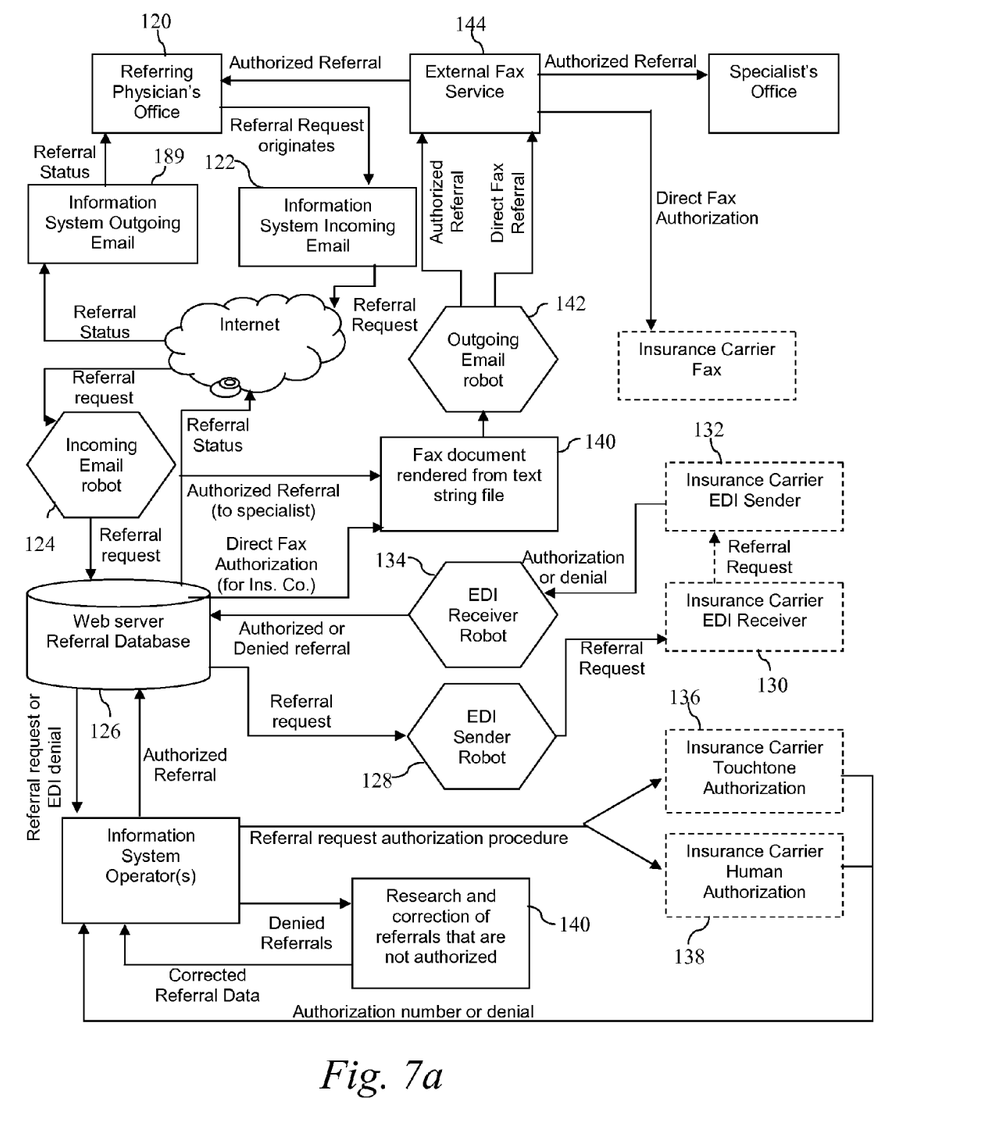
FIG. 7a is a state diagram showing referral request operations.

FIG. 7a illustrates a state diagram showing referral authorization. In referral authorization, a first healthcare provider, the "referring physician" refers a patient to a second physician, the "specialist". While the two healthcare providers are referred to herein as "referring physician" and "specialist", in actual practice, either or both of the physician's could be specialists or general practitioners. In many insurance plans, the specialist must be on an approved list of physicians under contract to the insurance company and, further, the referral must be approved prior to the appointment between the patient and the specialist for full insurance reimbursement. In state 120, the referring physician's office refers the patient to a specialist. To do so, the referring physician must know which specialists are available under a given insurance plan.

Figure 7B:
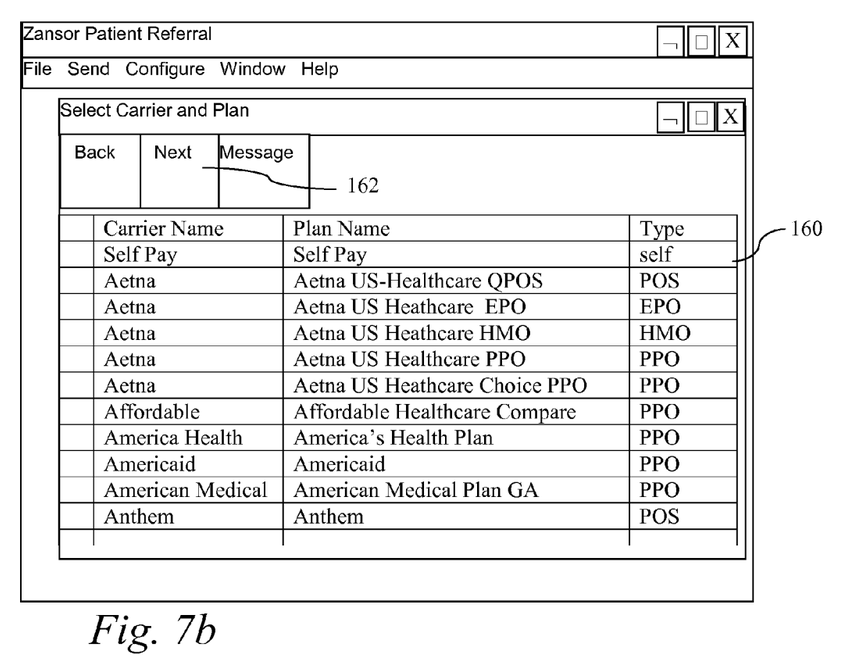
FIGS. 7b–7f are screen displays used in referral requests.
Figure 7C:
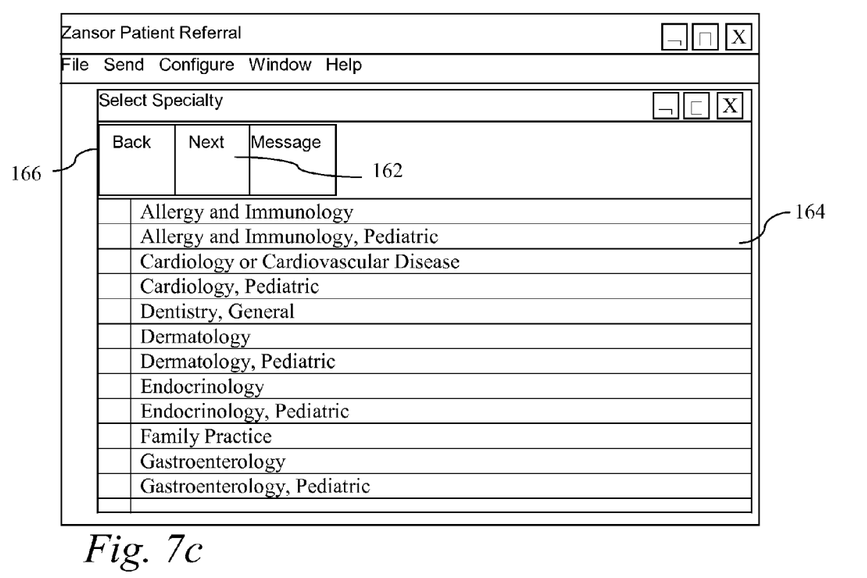
Figure 7D:
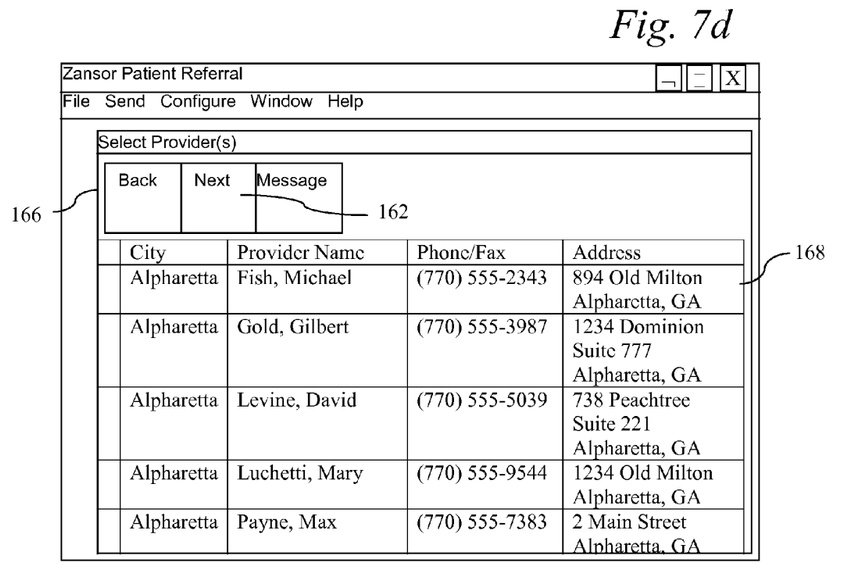

Referring to FIGS. 7b through 7e, a preferred embodiment for entering referral information using the healthcare information system program 24 is shown. In FIG. 7b, a list 160 of insurance plans is displayed by the healthcare information system 24 (if the patient information has been entered, the patient's plan will already be known). The patient's insurance plan is chosen from list 160 and the "Next" button 162 on the screen is pressed. As shown in FIG. 7c, responsive to the selected insurance plan, a list 164 of specialties is displayed. The desired specialty is chosen from list 164 and the Next button 162 is pressed again (the series of choices can be reversed and re-entered by pressing the "Back" button 166). Responsive to the selection of the specialty, a list 168 of specialists for the plan is displayed, as shown in FIG. 7d.

Figure 7E:
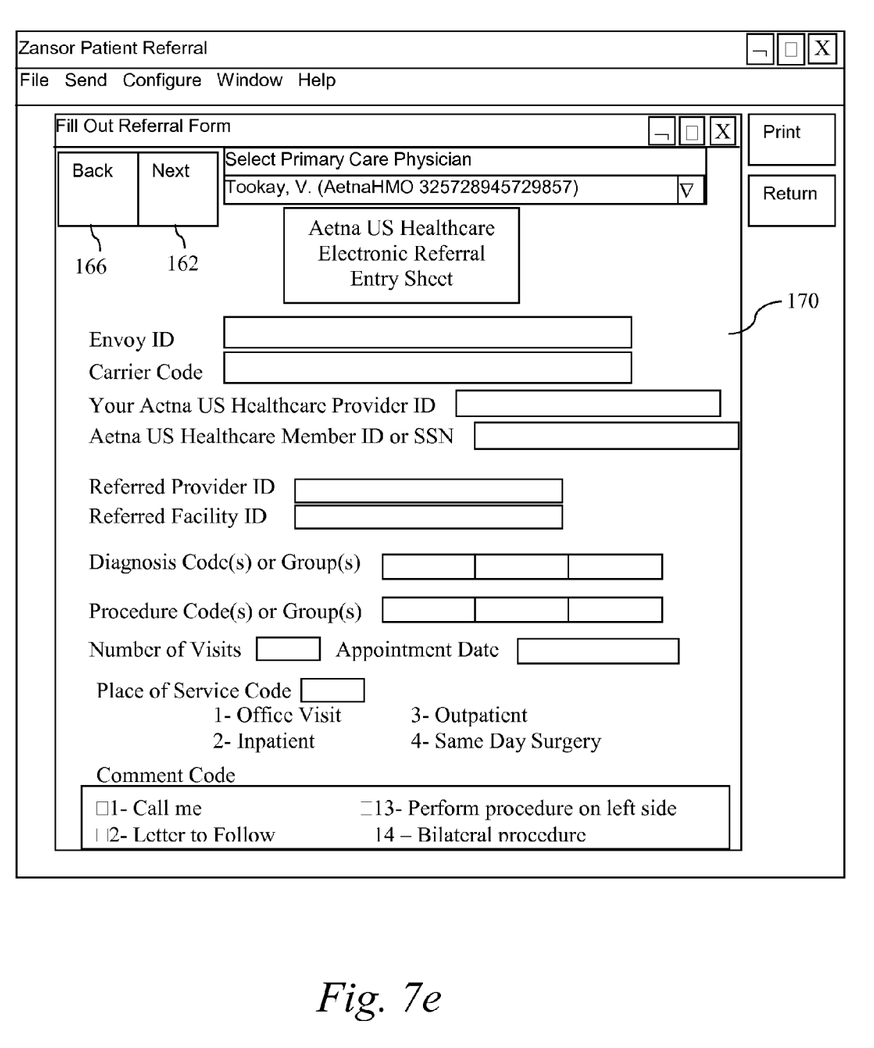

Selecting one of the specialists from the list 168 causes a form to be displayed. An exemplary form 170 is shown in FIG. 7e. In the preferred embodiment, the form displayed to the by the healthcare information system 24 has the same layout and fields as the form which would normally be filled in manually for a patient referral. The user may also choose to enter a specialist not found on the list by selecting the "unlisted" category and typing the specialist's name into the form. Selecting the "unlisted" category creates a seperate email message with the specialist name and plan name. This message is then researched and if the specialists approval by the plan is verified, he or she is added to the global database. The forms for the various insurance plans are kept in the forms database 23. Information for the patient, referring physician and the specialist are automatically filled by the healthcare information system responsive to data in the local database 22. Other information is filled in at the keyboard or by using pull-down menus, where appropriate.

Referring again to FIG. 7a, once the referral form is completed, it is sent by e-mail to the central information system 12 in state 122. Only the data from the fields of the form is sent in the e-mail, not the form itself, as will be discussed in greater detail hereinbelow. The e-mail progresses through the Internet and is retrieved by the e-mail robot 124 of the central information system 12. The e-mail robot checks for new e-mail periodically. The referral request is stored in the referral database 126.

If the insurance plan provides for EDI authorization, a referral request is sent by a EDI sender robot 128 which periodically checks the referral database 126 for referral requests which can be handled through EDI. The EDI sender robot sends the referral request to the appropriate insurance carrier EDI receiver 130, which replies with an authorization or denial through a corresponding insurance carrier EDI sender 132. The authorization/denial is passed through an EDI receiver robot 134 to the referral database 126.

If the referral request was denied in an EDI transaction or if the referral request cannot be made using an EDI transaction, it is passed to an operator/administrator associated with the central information system 12. Non-EDI referral requests are made by an operator/administrator using touchtone authorization 136 or by direct phone call to insurance company administrators 138. Authorized referrals are passed by the operator/administrator to the referral database. Denied referrals, either by EDI or manually, are researched and correcting entries are generated to update the global database 14 in step 140. In general, denials are caused by an incorrect patient ID number, referring physician ID number or specialist ID number.

Figure 7F:
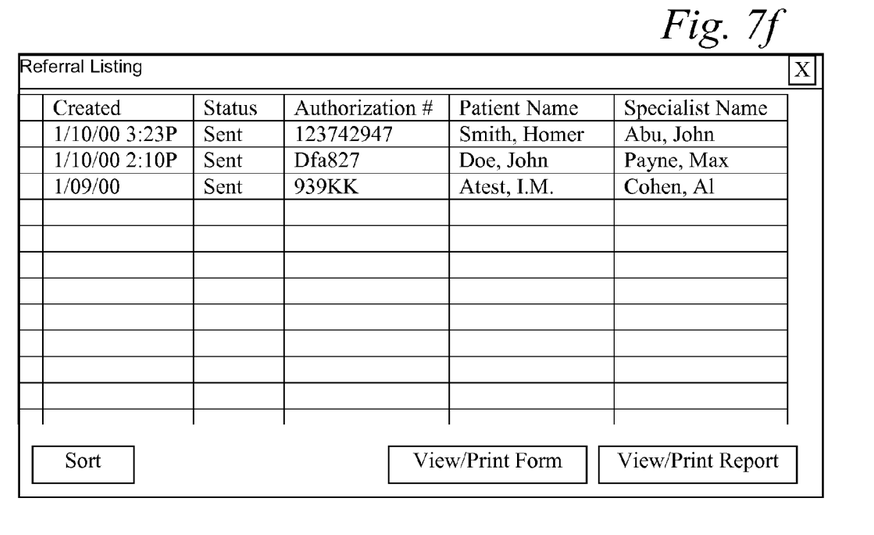

Referral status is sent to the local database 22 of the referring physician's office via e-mail in state 139. As described above, the information can be sent as an attachment to an e-mail message that is copied to the local database. The referring physician may review the status of referral requests, as shown in FIG. 7f. In addition, a fax of the authorized referrals is sent to both the referring physician's office and the specialist in state 140. Direct fax authorization requests are sent to the insurance company when this method is appropriate. In the preferred embodiment, an authorizing fax is generated and sent as an e-mail message via the outgoing e-mail robot 142 to an Internet fax service 144.

Figure 8:
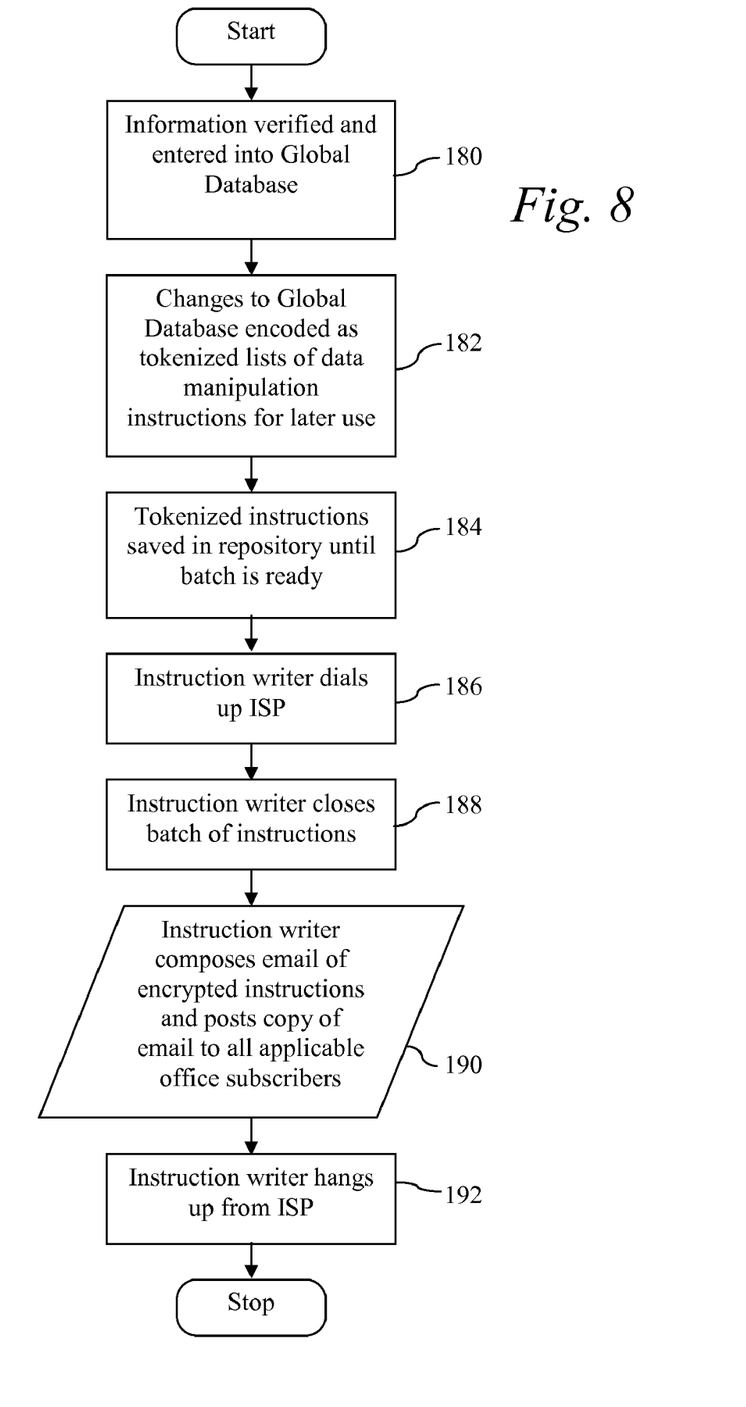
FIG. 8 is a flow chart describing operation of a SQL Update Routine.

FIG. 8 illustrates an SQL Update routine for updating the local databases 22 at each office 16. As shown above, information has been verified and entered into the global database throughout the day for eligibility and/or referral purposes as shown in block 180. Corresponding to the changed records, tokenized lists of data of SQL data manipulation instructions are generated in step 182 and are stored in the repository 32 until ready for sending to the offices 16 via e-mail (step 184). Since offices in different regions of the country will have different databases of insurance information, the SQL instructions will not be the same for all offices (assuming the network 10 spans multiple geographic regions). In step 186, the instruction writer routine accesses the Internet and closes the batch of instructions for transmittal in step 188. In step 190, the instruction writer routine composes the sets of SQL instructions and attaches them to e-mail messages to the offices 16. In step 192, the instruction writer routine disconnects from the Internet. These SQL instructions that are retrieved by the office download routine (see FIG. 2) to produce an updated local database 22 that is synchronized with the global database 14.

As discussed hereinabove, the preferred embodiment uses a graphical interface that allows healthcare personnel to enter and view information using electronic forms which replicate the paper forms provided by the insurance companies. Using standard forms reduces the learning curve in operating the healthcare information system 22. Forms may be revised, added and removed concurrent with the downloaded database updates. However, it is desirable to store and transmit information from the forms separate from the form itself.

The system uses a proprietary page definition language (PDL) to accurately render insurance forms in various ways. Using the actual images of the forms with which users are familiar is the best way to reduce the training curve and to protect the continuity of the overall business process during the transition from manual to electronic filing of referrals and eligibility requests. The ZFD (Zansor File Definition) file format described herein is used throughout the healthcare information network 10 to (1) render forms on-screen for display only, (2) render forms on-screen for editing and updating, (3) render forms for printing and (4) render forms for faxing. ZFD contains information about the form's layout, content, and content attributes. It is a full-featured single-page definition language.

ZFDs are text-only messages, and can be encrypted as other text can be encrypted to safeguard the information contained within to support ethical and business needs for confidentiality. They can be stored as-is in a database, or parsed and interpreted by applications in the healthcare information network 10. Because the insurance forms are important to the operation of the healthcare information network 10, many applications used in the healthcare information network 10 are equipped to read and interpret ZFDs in order to act on the information contained therein.

At its highest level, the ZFD format contains two sections: (1) page metadata—information about the form itself, applying to all parts of the form and (2) item metadata—individual data items on the form.

A sample of a form metadata file is listed below:
FormName=FamilyPlus
TimeStamp=08/29/1999 22:55:20
Version=1
ImageName=FamilyPlus.bmp
AuthModel=1
AuthPhoneNumber=404-315-3887
END The ZFD page metadata is a tagged data format, meaning that the data is preceded by a tag name and an equals sign, as shown above. This allows for quick and intelligent parsing of the page metadata, and provides flexibility in updates to the format, as the items are not position-dependent.

TABLE 1

Page Metadata

| Tag | Description | Notes |
|---|---|---|
| FormName | | A descriptive name given to each form for use in the user interface and internally. |
| TimeStamp | | Timestamp information allows tracking of the ZFD by time. |
| Version | ZFD version identifier | ZFDs may exist in various versions during the course of changes. This identifier canbe used to make decisions and process different versions differently. |
| ImageName | Name of image file on system | Rendering is done using actual images of the forms. Image data is not part of the ZFD, so as to save space and bandwidth. Each component that uses ZFDs subscribes to a subsystem which keeps forms and the referenced images in synchronization. |
| AuthModel | Authorization model identifier | Used by various parts of the system to provide intelligent routing of the referral/eligibility data based on pre-defined business models. Different requests, with different authorization models, can each be routed in an efficient and customized manner based on the value of this tag. |
| Auth-Phone-Number | Phone number to dial for the authorization | Later to be used by operator and supervisor auto-dialer utilities |
| END | | Terminates the page metadata |

The item metadata is a mixture of fixed- and variable-length data that is used to render and contain information about individual items that appear on forms.

TABLE 2

Item Metadata

| ELEMENT | Description | Notes |
|---|---|---|
| flags | fixed-length position-dependent text element | various one-character text items which identify the item in various ways; currently most of these flags are unused |
| ordinal 1 | order of the element on the form | used for ordering and re-ordering the element during rendering and editing |
| ordinal 2 | order of the element on the form | used for ordering and re-ordering the element during rendering and editing |
| left top width height | screen and paper positioning units, used for placing the item at the correct position for viewing and printing | |

TABLE 2-continued

Item Metadata

| ELEMENT | Description | Notes |
| --- | --- | --- |
| font name | Windows TrueType font name for rendering item | |
| font size | Windows TrueType font size for rendering item | |
| maximum length | maximum length for text input items | used for user-editable items only |
| category | integer identifying item's "category" for processing and rendering purposes | different categories are processed and differently, and many categories are used to tag the contents (q.v.) of the item so that the contents can be interpreted appropriately |
| registry section | section of the Windows registry entry from which this item comes | some data items come from the Windows registry, and this item allows the interpreting application to locate the correct Windows registry item |
| registry key | key of the Windows registry entry from which this item comes | some data items come from the Windows registry, and this item allows the interpreting application to locate the correct Windows registry item |
| contents | text | user's input, pre-defined output, and other data resides here and is read-only or read-write depending on the application interpreting the ZFD |
| END | | terminates the item metadata |

Figure 9:
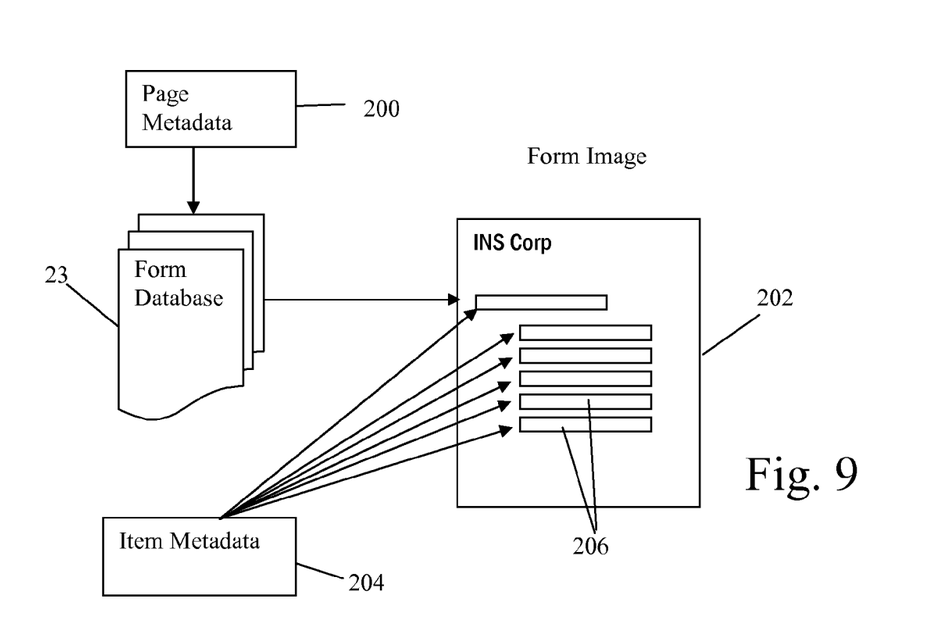
FIG. 9 is a diagram of a form used to input and display information.

FIG. 9 graphically illustrates the relationship between a form and the metadata files. The page metadata 200 points to a form image 202 in an associated form database 23. The image can be a bitmapped image or other image file type. The item metadata 204 defines the fields 206 and associated field contents (i.e., the data) to be mapped to the form image.

The metadata files can be easily stored and transmitted as a very compact file. Further, the files can be encrypted, if desired.

In the preferred embodiment, the data in the local database 22 is encrypted, for a number of reasons. First, encryption prevents the unauthorized viewing of patient information. Second, encryption prevents the databases, which may be in a standard database form, from being modified outside the healthcare information system program 24. Third, it prevents competitors from copying database information from a local database.

Encrypted information, however, can be difficult to search. In the present invention, searchable fields have a counterpart that is encoded in a many-to-one fashion. In the preferred embodiment, a Soundex encoding scheme is used.

The Soundex class of encoding schemes was developed to categorize names in a phonetic manner to provide fuzzy searches. The original Soundex encoding scheme used herein is based on that shown in Knuth, D. E., The Art of Computer Programming, Volume 3, page 392, Addison-Wesley Publishing Company (1973).

In the preferred embodiment, the Soundex fields in the database are not used to retrieve similarly phonetic names, but rather for hashing purposes. "Hashing" involves the "shrinking" of data into "containers" for faster retrieval. For example, if one can hash 1,000,000 names equally into 1,000 hash entries, then a search for a name involves two steps: (1) computing the hash value for the name and (2) looking for the name in the (very much smaller) container of 1,000 names. The resulting performance benefit is therefore on the order of 1,000-fold.

The original Soundex encoding scheme has been modified as described below to improve its usefulness in hashing data. In general, a more specific, adapted algorithm is used to provide five-character codes, which have been found to be significantly more accurate. The Soundex index is not used to do direct searches, but rather to create hashing containers that are then stored with the encrypted data. The result is that data stored in a strongly encrypted format can be quickly found and displayed.

The Visual Basic source code for encoding a Soundex5 field is set forth below:

```
Public Function Soundex5 (ByVal s As String)
    Const CODE="01230120022455012623010202" 'abc-
        defghijklmnopqrstuvwxyz
    Dim sKey As String * 5
    Dim i As Integer
    Dim c As String * 1
    Dim sLast As String * 1
    Dim x As Integer
    Dim iPos As Integer
    On Error GoTo ERR_Soundex
    skey="00000"
    sLast=""
    If Len(s)=0 Then
        Soundex5=sKey
        Exit Function
    End If
    s=UCase$(Trim$(s))
    For i=1 To Len(s)
        c=Mid$(s, i, 1)
        If c="," Then Exit For
        If c>="A" And c<="Z" Then
            x=Asc(c)-64
            c=Mid$(CODE, x, 1)
            If c<>sLast Then
                iPos=iPos+1
                Mid(sKey, iPos, 1)=c
                sLast=c
            End If
            If iPos=5 Then Exit For
        End If
    Next i
    Soundex5=sKey
    Exit Function
ERR_Soundex:
    Soundex5="00000"
    Exit Function
End Function
```

Figure 10:
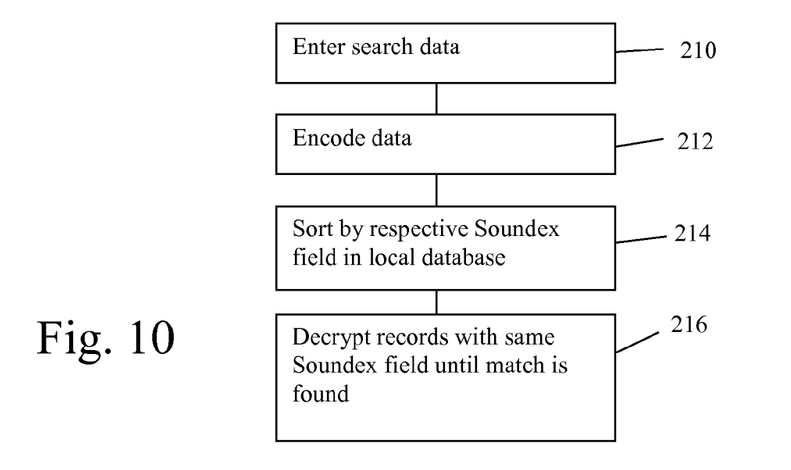
FIG. 10 is a flow chart describing a search routine for encrypted information.

A flow chart for retrieving data using the Soundex encoding is shown in FIG. 10. In step 210, the user inputs data into a search field, such as a patient or doctor name. In step 212, a five digit Soundex index is generated, per the method described above. In step 214, the corresponding table in the local database 22 is sorted based on a field that contains a Soundex index corresponding to the field for which the search is being performed. Records with a matching Soundex index are decrypted in step 216 until a matching record is found.

The present invention provides significant advantages over the prior art. First, if any healthcare provider in the network 10 encounters inaccuracies or omissions in the local database 22, that information is automatically uploaded to the central information system 12 for modification of the global database 14 after verification. Accordingly, each provider in the network benefits from the updates or corrections attributable to any provider in the network 10. As a result, highly accurate and up-to-date information is available to all healthcare providers for various purposes, including eligibility and benefits verification and referral authorization. Second, the electronic forms software provides an interface that is familiar to both the providers and the insurance companies, while maintaining a compact and secure data format. Third, the network significantly reduces the overhead, expense, and frustration associated with interacting with insurance companies for approvals of referrals and verification of eligibility. Fourth, a highly secure database is provided, while maintaining fast retrieval of information.

Although the Detailed Description of the invention has been directed to certain exemplary embodiments, various modifications of these embodiments, as well as alternative embodiments, will be suggested to those skilled in the art. The invention encompasses any modifications or alternative embodiments that fall within the scope of the Claims.

The invention claimed is:

1. A healthcare information system, comprising:
   a plurality of provider office systems, each provider office system comprising circuitry for generating referral requests with reference to a database associating insurance healthplans with doctors;
   referral authorization circuitry for:
      receiving said referral requests,
      generating electronic authorization requests to an associated insurance company responsive to ones of said referral requests,
      receiving an electronic authorizations/denial for each electronic authorization request;
      forwarding denied authorization requests to a third party human researcher for further research; and
      updating said database responsive to said research.

2. The healthcare information system of claim 1 wherein said referral authorization circuitry further forwards referral requests that cannot be authorized electronically to a third party human researcher.

3. The healthcare information system of claim 1 wherein said database comprises a central information system having a global database of referral information in communication with said provider office systems.

4. The healthcare information system of claim 1 wherein said authorization requests are EDI (electronic data interchange) messages.

5. A method of providing referral information, comprising the steps of:
   providing a database associating insurance healthplans with doctors;
   electronically receiving said referral requests generated by reference to said database from a plurality of provider office systems;
   generating electronic authorization requests to an associated insurance company responsive to ones of said referral requests;
   receiving an electronic authorization or denial in response to each electronic authorization request;
   forwarding denied requests to a third party human researcher for further research; and
   updating said database responsive to said research.

6. The method of claim 5 and further comprising the step of manually researching denied authorization requests.

7. The method of claim 6 and further comprising the step of manually researching referral requests that cannot be authorized electronically.

* * * * *